United States Patent
Carson et al.

(10) Patent No.: US 6,436,959 B1
(45) Date of Patent: *Aug. 20, 2002

(54) 4-[ARYL(PIPERIDIN-4-YL)] AMINOBENZAMIDES

(75) Inventors: John R. Carson, Norristown; Richard J. Carmosin, deceased, late of Quakertown, by Susan Carmosin, executrix; Louis J. Fitzpatrick, Souderton; Allen B. Reitz, Lansdale; Michele C. Jetter, Norristown, all of PA (US)

(73) Assignee: Ortho-McNeil Pharmaceutical, Inc., Raritan, NJ (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/220,189

(22) Filed: Dec. 23, 1998

(51) Int. Cl.⁷ .................. A61K 31/4468; C07D 213/72
(52) U.S. Cl. ........................ 514/326; 514/329; 546/224; 546/208
(58) Field of Search .................. 546/224, 186, 546/192, 207, 208; 514/318, 317, 326, 329, 332

(56) References Cited

FOREIGN PATENT DOCUMENTS

| EP | 383579 | 2/1990 |
| WO | WO 93/15062 | 2/1993 |
| WO | WO 96/36620 | 11/1996 |
| WO | WO 97/10230 | 3/1997 |
| WO | WO 97/23466 | 7/1997 |
| WO | 98/28270 | * 2/1998 |
| WO | WO 98/28270 | 7/1998 |
| WO | WO 98/28275 | 7/1998 |

* cited by examiner

*Primary Examiner*—Alan L. Rotman
*Assistant Examiner*—Rita Desai
(74) *Attorney, Agent, or Firm*—John Harbour

(57) ABSTRACT

4-[aryl(piperidin-4-yl)]aminobenzamides are delta-opioid receptor agonists/antagonists. As delta-opioid receptor agonists, such compounds are useful as analgesics. Depending on their agonist/antagonist effect, such compounds may also be useful immunosuppressants, antiinflammatory agents, agents for the treatment of mental illness, medicaments for drug and alcohol abuse, agents for treating gastritis and diarrhea, cardiovascular agents, and agents for the treatment of respiratory diseases.

8 Claims, No Drawings

4-[ARYL(PIPERIDIN-4-YL)] AMINOBENZAMIDES

The present invention relates to delta-opioid receptor agonists/antagonists. More particularly, the present invention relates to 4-[aryl(piperidin-4-yl)]aminobenzamides which are delta-opioid receptor agonists useful as analgesics.

BACKGROUND OF THE INVENTION

WO9723466 to Plobeck N. et al., discloses compounds (approximately) of the formula:

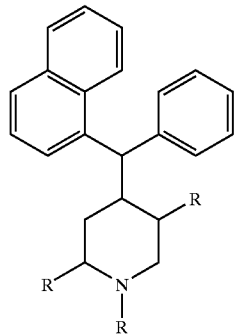

which are mu-opioid antagonists.

WO9636620 to Dondio G., discloses compounds (most relevantly) of the formula:

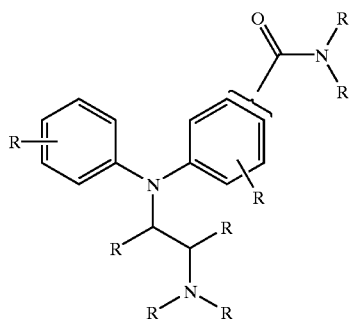

which are delta-opioid agonists/antagonists.

WO9710230 to Dondio G. et al., discloses compounds (most relevantly) of the formula:

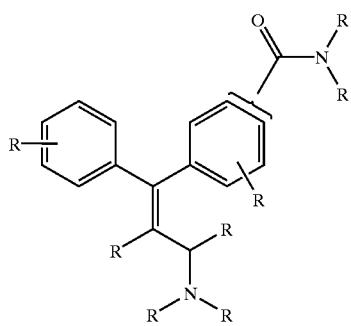

which are delta-opioid, kappa-opioid and mu-opioid receptor agonists/antagonists.

WO9315062 to Chang K. et al., discloses compounds (approximately) of the formula:

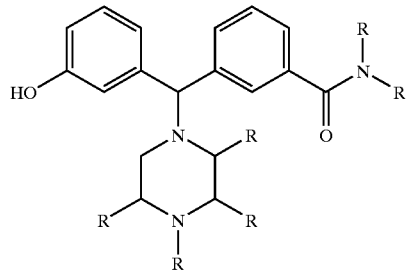

which are delta-opioid and mu-opioid receptor agonists.

It is an object of the present invention to provide delta-opioid receptor agonists as analgesics.

It is another object of the present invention to provide delta-opioid receptor selective agonists as analgesics having reduced side-effects.

It is another object of the present invention to provide delta-opioid receptor agonists/antagonists as immunosuppressants, antiinflammatory agents, agents for the treatment of mental illness, medicaments for drug and alcohol abuse, agents for treating gastritis and diarrhea, cardiovascular agents, and agents for the treatment of respiratory diseases.

It is another object of the present invention to provide delta-opioid receptor selective agonists/antagonists as immunosuppressants, antiinflammatory agents, agents for the treatment of mental illness, medicaments for drug and alcohol abuse, agents for treating gastritis and diarrhea, cardiovascular agents, and agents for the treatment of respiratory diseases, having reduced side-effects.

SUMMARY OF THE INVENTION

There are provided by the present invention delta-opioid receptor agonists/antagonists of the general formula:

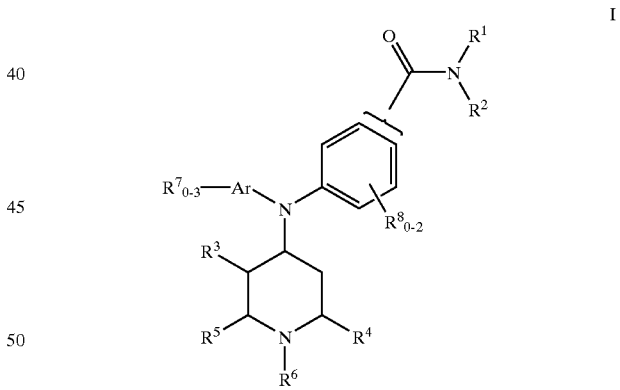

I where

Ar is phenyl, 1-naphthyl or 2-naphthyl, each optionally substituted with 1 to 3 $R^7$;

$R^1$ and $R^2$ are independently selected from the group consisting of hydrogen, $C_{1-8}$alkyl; phenyl, optionally mono-, di-, or tri-substituted with halo, $C_{1-6}$alkyl, $C_{1-6}$alkoxy or trifluoromethyl; or benzyl, optionally mono-, di-, or tri-substituted with halo, $C_{1-6}$alkyl, $C_{1-6}$alkoxy or trifluoromethyl, or alternatively, $R^1$ and $R^2$ are taken together with their N of attachment to form a ring which is selected from the group consisting of pyrrolidinyl, morpholinyl, piperidinyl and hexamethyleneiminyl, each said ring optionally substituted with 1 to 4 methyl groups;

$R^3$, $R^4$ and $R^5$ are independently selected from hydrogen and $C_{1-4}$alkyl;

$R^6$ is selected from the group consisting of hydrogen; $C_{1-8}$alkyl; $C_{3-6}$cycloalkyl$C_{1-3}$alkyl, $C_{3-6}$alkenyl; $C_{1-6}$alkoxy$C_{1-3}$alkyl; 4-$C_{1-4}$alkyl-4,5-dihydro-5-oxo-1H-tretrazol-1-yl$C_{1-4}$alkyl; thien-2-yl$C_{1-4}$alkyl; thien-3-yl$C_{1-4}$alkyl; furan-2-yl$C_{1-4}$alkyl; furan-3-yl $C_{1-4}$alkyl; pyrrol-2-yl$C_{1-4}$alkyl; pyrrol-3-yl$C_{1-4}$alkyl; pyridin-2-yl$C_{1-4}$alkyl; pyridin-3-yl$C_{1-4}$alkyl; pyridin-4-yl$C_{1-4}$alkyl; pyrazinyl$C_{1-4}$alkyl; pyrimidin-2-yl $C_{1-4}$alkyl; pyrimidin-4-yl$C_{1-4}$alkyl; pyrimidin-5-yl $C_{1-4}$alkyl; thiazol-2-yl$C_{1-4}$alkyl; thiazol-4-yl$C_{1-4}$alkyl; thiazol-5-yl$C_{1-4}$alkyl; oxazol-2-yl$C_{1-4}$alkyl oxazol-4-yl$C_{1-4}$alkyl; oxazol-5-yl$C_{1-4}$alkyl and phenyl$C_{1-4}$alkyl, where the foregoing thienyl, furanyl, pyrrolyl, thiazolyl and oxazolyl are optionlly mono-, di-, or tri-substituted with a non-fused $R^7$ and the foregoing pyridinyl, pyrazinyl, pyrimidinyl and phenyl is optionally mono-, di-, or tri-substituted with $R^7$;

$R^7$ is independently selected from the group consisting of hydroxy, halo, $C_{1-3}$alkyl, $C_{1-3}$alkoxy, $C_{1-3}$acyl, $C_{1-3}$acyloxy, cyano, amino, $C_{1-3}$acylamino, $C_{1-3}$alkylamino, di($C_{1-3}$alkyl)amino, $C_{1-3}$alkylthio, $C_{1-3}$alkylsulfonyl, trifluoromethyl and trifluoromethoxy, and two $R^7$ can together form a single fused moiety selected from the group consisting of —(CH$_2$)$_{3-5}$— and —O(CH$_2$)$_{1-3}$O— attached to adjacent carbon atoms of Ar; and $R^8$ is independently selected from the group consisting of halo, $C_{1-6}$alkyl, $C_{1-6}$alkoxy and trifluoromethyl.

As delta-opioid receptor agonists, such compounds are useful as analgesics. Depending on their agonist/antagonist effect, such compounds may also be useful immunosuppressants, antiiinflammantory agents, agents for treatment of mental illness, medicaments for drug and alcohol abuse, agents for treating gastritis and diarrhea, cardiovascular agents, and agents for the treatment of respiratory diseases.

DETAILED DESCRIPTION OF THE INVENTION

The core structure of the compounds of the present invention can be made in a two step process. This process must be modified as required by the strategy employed to obtain the various substituents. In a first strategy, the starting materials are substituted as desired with the final substituents and, where the substituents or their protected forms are stable to the reaction conditions, the core structure may be subsequently made by the two step process. In a second strategy, the final core structure is obtained and, where the core structure is stable to the modifying reaction conditions, the substituents are modified as desired. Variations might include modifying the substituents on intermdiates or replacing precursor substituents on the finished core structure.

Scheme A generally describes the manufacture of the compounds of the present invention. The first step of Scheme A is a reductive alkylation of piperidone A1 and amine A2 to produce N-aryl-piperidineamine A3. The reductive alkylation is carried out by combining the ketone A1, amine A2, and an appropriate solvent/reducing agent combination to form a reaction mixture which is cooled or heated as necessary. Suitable solvent/reducing agent combinations include 1,2-dichloroethane or acetonitrile/NaBH(OAc)$_3$+acid catalyst; methanol/NaBH$_3$CN+acid catalyst; methanol or ethanol or isopropanol/NaBH$_4$; or alcoholic solvent/H$_2$+ noble metal catalyst. The use of the 1,2-dichloroethane or acetonitrile/NaBH(OAc)$_3$+acid catalyst combination is further described by Abdel-Magid, A. F., et al., J. Org.Chem., Vol. 61, pp 3849–3862 (1996). In the second step of Scheme A, the N-aryl-piperidineamine A3 is reacted with a bromo, iodo or trifluoromethanesulfonyloxy substituted benzamide A4 in the presence of a palladium catalyst, phosphine ligand and base to give the (N-aryl, N-piperidin-4-yl) aminobenzamide. Preferred palladium catalysts include PdCl$_2$+phosphine ligand, tris(dibenzylideneacetone) dipalladium(0) which is Pd$_2$(dba)$_3$+phosphine ligand, Pd(OAc)$_2$+phosphine ligand and Pd(Ph$_3$P)$_4$(0). Suitable phosphine ligands include BINAP and tri(o-tolyl phosphine). Suitable bases include NaOtBu and Cs$_2$CO$_3$. The reaction of the second step is an arylation further described by Buchwald, S. L., J. Org. Chem., Vol. 61, p 1133 (1996). The manufacture of the various starting materials for Scheme A is well within the skill of persons versed in this art.

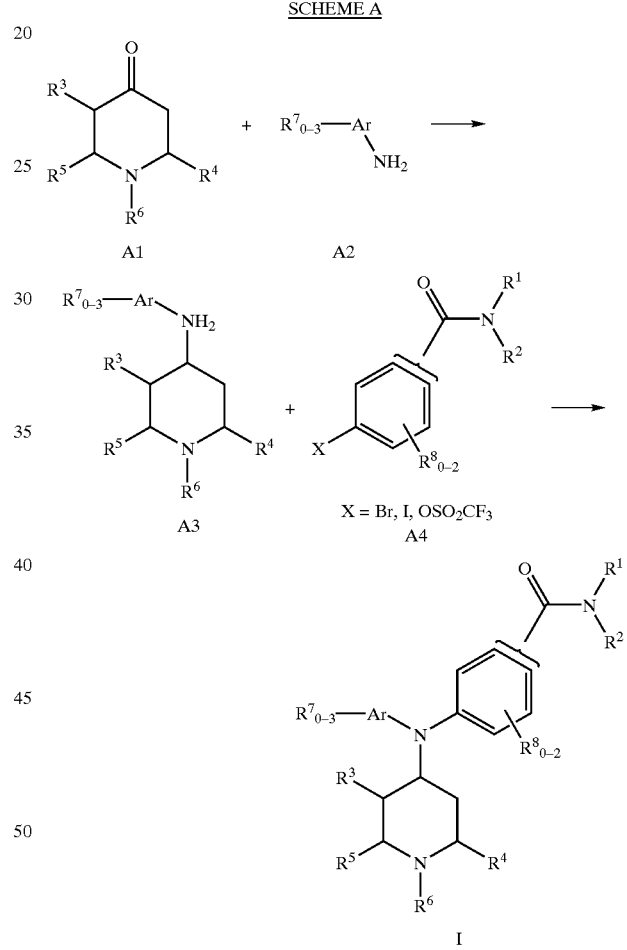

SCHEME A

Preferred Ar is phenyl.

Preferred $R^1$ and $R^2$ are independently selected from the group consisting of hydrogen, methyl, ethyl, n-propyl, i-propyl, n-butyl, t-butyl, i-butyl, phenyl, p-chlorophenyl, p-fluorophenyl, p-methylphenyl, p-trifluoromethylphenyl, benzyl, p-chlorobenzyl, p-fluorobenzyl, p-methylbenzyl and p-trifluoromethylbenzyl, or alternatively, preferred $R^1$ and $R^2$ are taken together with their N of attachment to form a ring which is selected from the group consisting of pyrrolidinyl and piperidinyl.

Preferred $R^3$, $R^4$ and $R^5$ are independently selected from hydrogen, methyl, ethyl, n-propyl, i-propyl and t-butyl.

Preferred $R^6$ are selected from the group consisting of hydrogen, methyl, ethyl, n-propyl, i-propyl, n-butyl, i-butyl, t-butyl, cyclopropylmethyl, ethenyl, allyl, methoxymethyl, benzyl, p-chlorobenzyl, p-fluorobenzyl, p-methylbenzyl, p-trifluoromethylbenzyl, p-aminobenzyl, thien-2-ylCH$_2$CH$_2$—, thien-3-ylCH$_2$CH$_2$—, pyridin-3-ylCH$_2$CH$_2$—, pyridin-4-ylCH$_2$CH$_2$—, thiazol-2-ylCH$_2$CH$_2$— and phenylCH$_2$CH$_2$—, any of which may be $R^7$ substituted as taught above. It is a preferred embodiment of $R^6$, that where it contains a phenyl or heteroaromatic group, that the moiety linking the phenyl or heteroaromatic group to the piperidinyl moiety be at least two carbon atoms long. Thus this linking moiety might be ethyl or propyl which is beta substituted with the phenyl or heteroaromatic group, or propyl, which is gamma substituted.

Preferred $R^7$ are independently selected from the group consisting of hydroxy, chloro, bromo, fluoro, methyl, ethyl, n-propyl, i-propyl, n-butyl, i-butyl, t-butyl, methoxy, ethoxy, formyl, acyl, acetoxy, cyano, amino, methylamido, methylamino, N,N-dimethylamino, methylthio, methylsulfonyl, trifluoromethoxy and trifluoromethyl, and preferred moieties where two $R^7$ together form a single moiety are selected from the group consisting of propylene, butylene and —OCH$_2$O—.

Preferred $R^8$ are independently selected from the group consisting of chloro, bromo, fluoro, methyl, ethyl, n-propyl, i-propyl, t-butyl, methoxy, ethoxy and trifluoromethyl.

Preferred compounds of the present invention have the general structure:

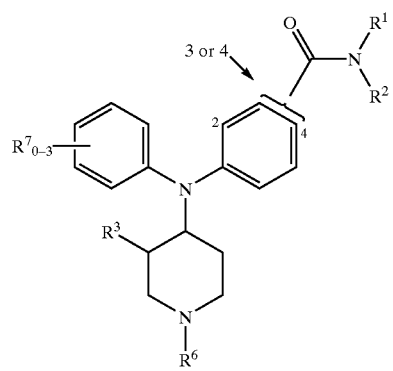

where $R^1$, $R^2$, $R^3$, $R^6$ and $R^7$ are dependently selected from the groups consisting of:

| Cpd # | $R^7$ | $R^6$ | $R^1$ | $R^2$ | amide subst. | $R^3$ |
|---|---|---|---|---|---|---|
| P1 | none | —CH$_2$CH=CH$_2$ | —CH$_2$CH$_3$ | —CH$_2$CH$_3$ | 4 | H |
| P2 | none | —CH$_2$—◁ | —CH$_2$CH$_3$ | —CH$_2$CH$_3$ | 4 | R |
| P3 | 3-OH | —CH$_2$CH=CH$_2$ | —CH$_2$CH$_3$ | —CH$_2$CH$_3$ | 4 | H |
| P4 | 3-OH | —CH$_2$—◁ | —CH$_2$CH$_3$ | —CH$_2$CH$_3$ | 4 | H |
| P5 | 3-OH | —CH$_3$ | —CH$_2$CH$_3$ | —CH$_2$CH$_3$ | 4 | H |
| P6 | 3-OH | —CH$_2$CH$_3$ | —CH$_2$CH$_3$ | —CH$_2$CH$_3$ | 4 | H |
| P7 | 3-OH | —CH$_2$CH$_2$Ph | —CH$_2$CH$_3$ | —CH$_2$CH$_3$ | 4 | H |
| P8 | 3-OH | —CH$_3$ | -nC$_3$H$_7$ | -nC$_3$H$_7$ | 4 | H |
| P9 | 3-OH | —CH$_2$CH$_3$ | -nC$_3$H$_7$ | -nC$_3$H$_7$ | 4 | H |
| P10 | 3-OH | —CH$_2$CH$_2$Ph | -nC$_3$H$_7$ | -nC$_3$H$_7$ | 4 | H |
| P11 | 3-OH | —CH$_3$ | -nC$_4$H$_9$ | -nC$_4$H$_9$ | 4 | H |
| P12 | 3-OH | —CH$_2$CH$_3$ | -nC$_4$H$_9$ | -nC$_4$H$_9$ | 4 | H |
| P13 | 3-OH | —CH$_2$CH$_2$Ph | -nC$_4$H$_9$ | -nC$_4$H$_9$ | 4 | H |
| P14 | none | —CH$_3$ | -nC$_4$H$_9$ | -nC$_4$H$_9$ | 4 | H |
| P15 | none | —CH$_2$CH$_3$ | -nC$_4$H$_9$ | -nC$_4$H$_9$ | 4 | H |
| P16 | none | —CH$_2$CH$_2$Ph | -nC$_4$H$_9$ | -nC$_4$H$_9$ | 4 | H |
| P17 | 3-F | —CH$_3$ | -nC$_4$H$_9$ | -nC$_4$H$_9$ | 4 | H |
| P18 | 3-F | —CH$_2$CH$_3$ | -nC$_4$H$_9$ | -nC$_4$H$_9$ | 4 | H |
| P19 | 3-F | —CH$_2$CH$_2$Ph | -nC$_4$H$_9$ | -nC$_4$H$_9$ | 4 | H |
| P20 | 3-OCH$_3$ | —CH$_3$ | -nC$_4$H$_9$ | -nC$_4$H$_9$ | 4 | H |
| P21 | 3-OCH$_3$ | —CH$_2$CH$_3$ | -nC$_4$H$_9$ | -nC$_4$H$_9$ | 4 | H |
| P22 | 3-OCH$_3$ | -nC$_4$H$_9$ | -nC$_4$H$_9$ | -nC$_4$H$_9$ | 4 | H |
| P23 | 3,4-OCH$_2$O— | -nC$_3$H$_7$ | —CH$_2$CH$_3$ | —CH$_2$CH$_3$ | 4 | H |
| P24 | 3,4-OCH$_2$O— | -nC$_3$H$_7$ | -nC$_3$H$_7$ | -nC$_3$H$_7$ | 4 | H |
| P25 | 3,4-OCH$_2$O— | -nC$_3$H$_7$ | 2-C$_3$H$_7$ | 2-C$_3$H$_7$ | 4 | H |
| P26 | 3,4-OCH$_2$O— | -nC$_3$H$_7$ | -nC$_4$H$_9$ | -nC$_4$H$_9$ | 4 | H |
| P27 | 3-N(CH$_3$)$_2$ | -nC$_3$H$_7$ | —CH$_2$CH$_3$ | —CH$_2$CH$_3$ | 4 | H |
| P28 | 3-N(CH$_3$)$_2$ | -nC$_3$H$_7$ | -nC$_3$H$_7$ | -nC$_3$H$_7$ | 4 | H |
| P29 | 3-N(CH$_3$)$_2$ | -nC$_3$H$_7$ | 2-C$_3$H$_7$ | 2-C$_3$H$_7$ | 4 | H |
| P30 | 3-N(CH$_3$)$_2$ | -nC$_3$H$_7$ | -nC$_4$H$_9$ | -nC$_4$H$_9$ | 4 | H |
| P31 | 4-F | -nC$_3$H$_7$ | —CH$_2$CH$_3$ | —CH$_2$CH$_3$ | 4 | H |
| P32 | 4-F | -nC$_3$H$_7$ | -nC$_3$H$_7$ | -nC$_3$H$_7$ | 4 | H |
| P33 | 4-F | -nC$_3$H$_7$ | 2-C$_3$H$_7$ | 2-C$_3$H$_7$ | 4 | H |
| P34 | 4-F | -nC$_3$H$_7$ | -nC$_4$H$_9$ | -nC$_4$H$_9$ | 4 | H |
| P35 | 2-F | -nC$_3$H$_7$ | —CH$_2$CH$_3$ | —CH$_2$CH$_3$ | 4 | H |
| P36 | 2-F | -nC$_3$H$_7$ | -nC$_3$H$_7$ | -nC$_3$H$_7$ | 4 | H |
| P37 | 2-F | -nC$_3$H$_7$ | 2-C$_3$H$_7$ | 2-C$_3$H$_7$ | 4 | H |
| P38 | 2-F | -nC$_3$H$_7$ | -nC$_4$H$_9$ | -nC$_4$H$_9$ | 4 | H |

-continued

| Cpd # | R⁷ | R⁶ | R¹ | R² | amide subst. | R³ |
|---|---|---|---|---|---|---|
| P39 | 3-Cl, 4-OCH₃ | -nC₃H₇ | —CH₂CH₃ | —CH₂CH₃ | 4 | H |
| P40 | 3-Cl, 4-OCH₃ | -nC₃H₇ | -nC₃H₇ | -nC₃H₇ | 4 | H |
| P41 | 3-Cl, 4-OCH₃ | -nC₃H₇ | 2-C₃H₇ | 2-C₃H₇ | 4 | H |
| P42 | 3-Cl, 4-OCH₃ | -nC₃H₇ | -nC₄H₉ | -nC₄H₉ | 4 | H |
| P43 | 3-CF₃ | -nC₃H₇ | —CH₂CH₃ | —CH₂CH₃ | 4 | H |
| P44 | 3-CF₃ | -nC₃H₇ | -nC₃H₇ | -nC₃H₇ | 4 | H |
| P45 | 3-CF₃ | -nC₃H₇ | 2-C₃H₇ | 2-C₃H₇ | 4 | H |
| P46 | 3-CF₃ | -nC₃H₇ | -nC₄H₉ | -nC₄H₉ | 4 | H |
| P47 | 3-OCH₃, 5-OCH₃ | -nC₃H₇ | —CH₂CH₃ | —CH₂CH₃ | 4 | H |
| P48 | 3-OCH₃, 5-OCH₃ | -nC₃H₇ | -nC₃H₇ | -nC₃H₇ | 4 | H |
| P49 | 3-OCH₃, 5-OCH₃ | -nC₃H₇ | 2-C₃H₇ | 2-C₃H₇ | 4 | H |
| P50 | 3-OCH₃, 5-OCH₃ | -nC₃H₇ | -nC₄H₉ | -nC₄H₉ | 4 | H |
| P51 | 3-CH₃ | -nC₃H₇ | —CH₂CH₃ | —CH₂CH₃ | 4 | H |
| P52 | 3-CH₃ | -nC₃H₇ | -nC₃H₇ | -nC₃H₇ | 4 | H |
| P53 | 3-CH₃ | -nC₃H₇ | 2-C₃H₇ | 2-C₃H₇ | 4 | H |
| P54 | 3-CH₃ | -nC₃H₇ | -nC₄H₉ | -nC₄H₉ | 4 | H |
| P55 | 4-CH₃ | -nC₃H₇ | —CH₂CH₃ | —CH₂CH₃ | 4 | H |
| P56 | 4-CH₃ | -nC₃H₇ | -nC₃H₇ | -nC₃H₇ | 4 | H |
| P57 | 4-CH₃ | -nC₃H₇ | 2-C₃H₇ | 2-C₃H₇ | 4 | H |
| P58 | 4-CH₃ | -nC₃H₇ | -nC₄H₉ | -nC₄H₉ | 4 | H |
| P59 | 2-CH₃, 3-CH₃ | -nC₃H₇ | —CH₂CH₃ | —CH₂CH₃ | 4 | H |
| P60 | 2-CH₃, 3-CH₃ | -nC₃H₇ | -nC₃H₇ | -nC₃H₇ | 4 | H |
| P61 | 2-CH₃, 3-CH₃ | -nC₃H₇ | 2-C₃H₇ | 2-C₃H₇ | 4 | H |
| P62 | 2-CH₃, 3-CH₃ | -nC₃H₇ | -nC₄H₉ | -nC₄H₉ | 4 | H |
| P63 | 3-OCF₃ | -nC₃H₇ | —CH₂CH₃ | —CH₂CH₃ | 4 | H |
| P64 | 3-OCF₃ | -nC₃H₇ | -nC₃H₇ | -nC₃H₇ | 4 | H |
| P65 | 3-OCF₃ | -nC₃H₇ | 2-C₃H₇ | 2-C₃H₇ | 4 | H |
| P66 | 3-OCF₃ | -nC₃H₇ | -nC₄H₉ | -nC₄H₉ | 4 | H |
| P67 | 3-SCH₃ | -nC₃H₇ | —CH₂CH₃ | —CH₂CH₃ | 4 | H |
| P68 | 3-SCH₃ | -nC₃H₇ | -nC₃H₇ | -nC₃H₇ | 4 | H |
| P69 | 3-SCH₃ | -nC₃H₇ | 2-C₃H₇ | 2-C₃H₇ | 4 | H |
| P70 | 3-SCH₃ | -nC₃H₇ | -nC₄H₉ | -nC₄H₉ | 4 | H |
| P71 | none | —CH₂Ph | —CH₂CH₃ | —CH₂CH₃ | 4 | ci-Me |
| P72 | none | —H | —CH₂CH₃ | —CH₂CH₃ | 4 | ci-Me |
| P73 | none | —CH₂CH═CH₂ | —CH₂CH₃ | —CH₂CH₃ | 4 | ci-Me |
| P74 | none | -nC₃H₇ | —CH₂CH₃ | —CH₂CH₃ | 4 | ci-Me |
| P75 | 3-OCH₃ | —CH₂Ph | —CH₂CH₃ | —CH₂CH₃ | 4 | ci-Me |
| P76 | 3-OCH₃ | —H | —CH₂CH₃ | —CH₂CH₃ | 4 | ci-Me |
| P77 | 3-OCH₃ | —CH₂CH═CH₂ | —CH₂CH₃ | —CH₂CH₃ | 4 | ci-Me |
| P78 | 3-OCH₃ | -nC₃H₇ | —CH₂CH₃ | —CH₂CH₃ | 4 | ci-Me |
| P79 | none | —CH₂Ph | —CH₂CH₃ | —CH₂CH₃ | 4 | tr-Me |
| P80 | none | —H | —CH₂CH₃ | —CH₂CH₃ | 4 | tr-Me |
| P81 | none | —CH₂CH═CH₂ | —CH₂CH₃ | —CH₂CH₃ | 4 | tr-Me |
| P82 | none | -nC₃H₇ | —CH₂CH₃ | —CH₂CH₃ | 4 | tr-Me |
| P83 | none | -nC₃H₇ | —CH₂CH₃ | —CH₂CH₃ | 4 | H |
| P84 | none | -nC₃H₇ | -nC₃H₇ | -nC₃H₇ | 3 | H |
| P85 | none | -nC₃H₇ | —CH₂Ph | —CH₂CH₃ | 3 | H |
| P86 | none | -nC₃H₇ | —(CH₂)₅— | | 3 | H |
| P87 | *2,3-CH═CHCH═CH— | -nC₃H₇ | —CH₂CH₃ | —CH₂CH₃ | 3 | H |
| P88 | *2,3-CH═CHCH═CH— | -nC₃H₇ | -nC₃H₇ | -nC₃H₇ | 4 | H |
| P89 | 3,4-(CH₂)₄— | -nC₃H₇ | —CH₂CH₃ | —CH₂CH₃ | 4 | H |
| P90 | 3,4-(CH₂)₄— | -nC₃H₇ | -nC₃H₇ | -nC₃H₇ | 4 | H |
| P91 | 3,4-CH₂CH₂CH₂— | -nC₃H₇ | —CH₂CH₃ | —CH₂CH₃ | 4 | H |
| P92 | 3,4-CH₂CH₂CH₂— | -nC₃H₇ | -nC₃H₇ | -nC₃H₇ | 4 | H |
| P93 | none | 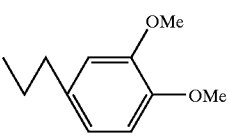 | —CH₂CH₃ | —CH₂CH₃ | 4 | H |
| P94 | m-F | 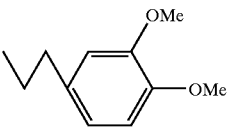 | —CH₂CH₃ | —CH₂CH₃ | 4 | H |
| P95 | m-sCH₃ | 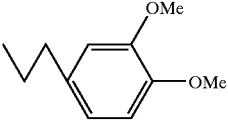 | —CH₃ | —CH₂CH₃ | 4 | ci-Me |

-continued

| Cpd # | R⁷ | R⁶ | R¹ | R² | amide subst. | R³ |
|---|---|---|---|---|---|---|
| P96 | none | benzo[1,3]dioxole-CH₂- | —CH₂CH₃ | —CH₂CH₃ | 4 | H |
| P97 | m-oCH₃ | benzo[1,3]dioxole-CH₂- | -nC₃H₇ | -nC₃H₇ | 4 | H |
| P98 | m-OH | benzo[1,3]dioxole-CH₂- | —CH₃ | —CH₂CH₃ | 4 | tr-Me |
| P99 | none | thiophene-CH₂- | —CH₂CH₃ | —CH₂CH₃ | 4 | H |
| P100 | o-F | thiophene-CH₂- | -nC₃H₇ | -nC₃H₇ | 4 | H |
| P101 | o-CH₃ | thiophene-CH₂- | —CH₃ | —CH₂CH₃ | 4 | ci-Me |
| P102 | none | 2-fluorophenyl-CH₂- | —CH₂CH₃ | —CH₂CH₃ | 4 | H |
| P103 | p-OH | 2-fluorophenyl-CH₂- | —CH₂CH₃ | -nC₃H₇ | 4 | H |
| P104 | p-F | 2-fluorophenyl-CH₂- | -nC₃H₇ | -nC₃H₇ | 4 | tr-Me |
| P105 | none | pyridine-CH₂- | —CH₂CH₃ | —CH₂CH₃ | 4 | H |
| P106 | m-sCH₃ | pyridine-CH₂- | -nC₃H₇ | -nC₃H₇ | 4 | H |
| P107 | m-OCF₃ | pyridine-CH₂- | —CH₃ | -nC₃H₇ | 4 | ci-Me |

-continued

| Cpd # | R⁷ | R⁶ | R¹ | R² | amide subst. | R³ |
|---|---|---|---|---|---|---|
| P108 | none | naphthyl-CF₃ | —CH₂CH₃ | —CH₂CH₃ | 4 | H |
| P109 | m-CH₃ | naphthyl-CF₃ | —CH₃ | —CH₂CH₃ | 4 | H |
| P110 | 2,3-oCH₃ | naphthyl-CF₃ | —CH₃ | -nC₃H₇ | 4 | H |

*Ar = naphthyl is depicted as R⁷ for convenience

The compounds of the present invention may be used to treat mild to moderately severe pain in warm-blooded animals, such as, humans by administration of an analgesically effective dose. The dosage range would be from about 1 to 3000 mg, in particular about 10 to 1000 mg or about 25 to 500 mg, of active ingredient 1 to 4 times per day for an average (70 kg) human although it is apparent that activity of individual compounds of the invention will vary as will the pain being treated. In regards to the use of these compounds as immunosuppressants, antiinflammatory agents, agents for the treatment of mental illness, medicaments for drug and alcohol abuse, agents for treating gastritis and diarrhea, cardiovascular agents, and agents for the treatment of respiratory diseases, a therapeutically effective dose can be determined by persons skilled in the art by use of established animal models. Such dosage would likely fall in the range of from about 1 to 3000 mg of active ingredient 1 to 4 times per day for an average (70 kg) human. Pharmaceutical compositions of the invention comprise the formula (I) compounds as defined above, particularly in admixture with a pharmaceutically-acceptable carrier.

To prepare the pharmaceutical compositions of this invention, one or more compounds of the invention or salt thereof as the active ingredient, is intimately admixed with a pharmaceutical carrier according to conventional pharmaceutical compounding techniques, which carrier may take a wide variety of forms depending of the form of preparation desired for administration, e.g., oral or parenteral such as intramuscular. In preparing the compositions in oral dosage form, any of the usual pharmaceutical media may be employed. Thus, for liquid oral preparations, such as for example, suspensions, elixirs and solutions, suitable carriers and additives include water, glycols, oils, alcohols, flavoring agents, preservatives, coloring agents and the like, for solid oral preparations such as, for example, powders, capsules and tablets, suitable carriers and additives include starches, sugars, diluents, granulating agents, lubricants binders, disintegrating agents and the like. Because of their ease in administration, tablets and capsules represent the most advantageous oral dosage unit form, in which case solid pharmaceutical carriers are obviously employed. If desired, tablets may be sugar coated or enteric coated by standard techniques. For parenterals, the carrier will usually comprise sterile water, through other ingredients, for example, for purposes such as aiding solubility or for preservation, may be included. Injectable suspensions may also be prepared, in which case appropriate liquid carriers, suspending agents and the like may be employed. The pharmaceutical compositions herein will contain, per dosage unit, e.g., table, capsule, powder, injection, teaspoonful and the like, and amount of the active ingredient necessary to deliver and effective dose as described above.

The pharmaceutically acceptable salts referred to above generally take a form in which the nitrogen of the piperidinyl ring is protonated with an inorganic or organic acid. Representative organic or inorganic acids include hydrochloric, hydrobromic, hydroiodic, perchloric, sulfuric, nitric, phosphoric, acetic, propionic, glycolic, lactic, succinic, maleic, fumaric, malic, tartaric, citric, benzoic, mandelic, methanesulfonic, hydroxyethanesulfonic, benezenesulfonic, oxalic, pamoic, 2-naphthalenesulfonic, p-toluenesulfonic, cyclohexanesulfamic, salicylic or saccharic.

The following examples are offered by way of illustration and not by way of limitation.

EXAMPLES

Procedure A

N-(3-Methoxyphenyl)-1-propyl-4-piperidinamine, I1

A solution of 4.5 mL (30 mmol) of N-propyl-4-piperidone, 3.4 mL (30 mmol) of m-anisidine, and 1.7 mL (30 mmol) of glacial acetic acid was stirred in 120 mL of 1,2-dichloroethane (DCE) and 9.49 g (45 mmol) of sodium triacetoxyborohydride was added. The solution was stirred at 25° C. for 3 h. The solution was washed with NaHCO₃ solution and brine. It was dried and the solvent was evaporated. The m-anisidine excess was distilled off in a Kugelrohr at 100° C./0.05 Torr. There was obtained 3.5 g (47% yield) of N-(3-methoxyphenyl)-1-propyl-4-piperidinamine as a solid. MS m/z=249 (M⁺+H). 300 MHz ¹H NMR (CDCl₃) δ7.1 (t, 1H); 6.15–6.35 (m, 3H); 3.75 (s, 3H ); 3.25 (m, 1H); 2.9 (m, 2H); 2.3 (m, 2H); 2.15 (m, 4H); 1.5 (m, 4H); 0.9 (t, 3H). Anal calcd. for $C_{15}H_{24}N_2O$; C, 72.54; H, 9.74; N, 11.28. Found: C, 72.55; H, 9.51; N, 11.21.

Example 1

N,N-Diethyl-4-[3-methoxyphenyl(1-propylpiperidin-4-yl)amino]benzamide Fumarate [1:1], C1

A solution of 3.5 g (14.1 mmol) of N-(3-methoxyphenyl)-1-propyl-4-piperidinamine, 3.61 g (14.1 mmol) of N,N- diethyl-4-bromobenzamide, 129 mg (0.141 mmol) tris (dibenzylideneacetone)-dipalladium(0) (Pd$_2$dba$_3$), 263 mg (0.423 mmol) of (R)-(+)-2,2'-bis(diphenylphosphino)-1,1'-binapthyl (+BINAP) and 1.89 g (19.7 mmol) of sodium t-butoxide in 25 mL of dry toluene was heated at 110° C. under Ar in a pressure vessel for 16 h. The mixture was cooled and partitioned between CH$_2$Cl$_2$ and H$_2$O. The organic layer was washed with brine, dried (K$_2$CO$_3$) and the solvent was evaporated. The residue was chromatographed on a Biotage Flash 75 unit using CH$_2$Cl$_2$:MeOH:NH$_4$OH, 92:8:0.8 as eluent. There was obtained 3.2 g (53% yield) of N,N-diethyl-4-[3-methoxyphenyl(1-propylpiperidin-4yl)amino]benzamide as a solid. A fumarate salt was prepared out of 2-PrOH: mp 168–169° C. MS m/z=424 (M$^+$+H). 300 MHz $^1$H NMR (DMSO-d$_6$) δ7.3 (t, 1H); 7.2 (d, 2H); 6.8 (d, 1H); 6.6 (m, 4H); 6.5 (s, 2H); 4.0 (m, 1H); 3.75 (s, 3H); 3.3 (q, 4H); 3.1 (d, 2H); 2.4 (m, 4H); 1.9 (d, 2H); 1.4 (m, 4H); 1.1 (t, 6H); 0.8 (t, 3H). Anal calcd. for C$_{26}$H$_{37}$N$_3$O$_2$.C$_4$H$_4$O$_4$: C, 66.77; H, 7.65; N, 7.78. Found: C, 66.69; H, 7.76; N 7.68.

Example 2

N,N-Diethyl-4-[3-hydroxyphenyl(1-propylpiperidin-4-yl)amino]benzamide Oxalate Hydrate [1.0:0.5:0.25], C2

A solution of 1.24 g (2.93 mmol) of N,N-diethyl-4-[3-methoxyphenyl(1-propylpiperidin-4-yl)amino]benzamide, C1, in 5 mL of CH$_2$Cl$_2$ was cooled to −60° C. under Ar and a solution of 17.58 mL (17.58 mmol) of 1.0 M BBr$_3$ in CH$_2$Cl$_2$ was added dropwise. The temperature was allowed to rise to 25° C. and the mixture was stirred for 18 h. It was partitioned between NaHCO$_3$ solution and 25% EtOH in CH$_2$Cl$_2$. The organic layer was dried (Na$_2$SO$_4$) and the solvent evaporated. The residue was was heated under reflux in 100 mL of saturated NaHCO$_3$ solution. The solution was cooled and extracted with CH$_2$Cl$_2$. The solution was dried (Na$_2$SO$_4$) and concentrated to give 1.1 g (92% yield) of N,N-diethyl-4-[3-hydroxyphenyl(1-propylpiperidin-4-yl) amino]benzamide as a gum. An oxalate salt was prepared in CH$_3$CN, mp 196–197° C. MS m/z=410 (M$^+$+H). 300 MHz $^1$H NMR (DMSO-d$_6$) δ7.2(m, 3H); 6.6 (m, 3H); 6.5(d, 1H); 6.4(s, 1H); 4.1(m, 1H); 3.3(q, 4H); 3.2 (m, 2H); 2.6 (m, 4H); 2.1 (d, 2H); 1.5 (m, 4H); 1.1 (t, 6H); 0.8 (t, 3H). Anal calcd. for C$_{25}$H$_{35}$N$_3$O$_2$.0.5 C$_2$H$_2$O$_4$.0.25 H$_2$O: C, 68.03; H, 8.01; N, 915; H$_2$O, 0.98. Found: C, 67.73; H, 7.73; N, 9.11; H$_2$O, 0.46.

Example 3

N,N-Diethyl-4-[phenyl(1-propylpiperidin-4-yl)amino]benzamide Fumarate[1:1], C3

Following the protocol of Procedure A and employing aniline in place of m-anisidine, N-phenyl-1-propyl-4-piperidinamine as obtained as a solid: mp 71–72° C. MS m/z=217 (M$^+$+H). 300 MHz $^1$H NMR (CDCl$_3$) δ7.1 (t, 2H); 6.65–6.5 (m, 3H); 3.5 (s, 1H); 3.25 (m, 1H); 3.3 (m, 1H) 2.9 (m, 2H); 2.3 (m, 2H); 2.15 (m, 4H); 1.5 (m, 4H); 0.9 (t, 3H).

Then, following the procedure of Example 1 and employing N-phenyl-1-propyl-4-piperidinamine in place of N-(3-methoxyphenyl)-1-propyl-4-piperidinamine, N,N-diethyl-4-[phenyl(1-propylpiperidine-4-yl)amino]benzamide fumarate was obtained as the product: mp 152–154° C. MS m/z=394 (M$^+$+H). 300 MHz $^1$H NMR (DMSO-d$_6$) δ7.45 (t, 2H); 7.3(t, 1H); 7.2 (d, 2H); 7.05 (d, 2H); 6.55 (d, 2H); 6.5 (s, 2H); 4.0 (m, 1H); 3.3 (q, 4H); 3.1 (d, 2H); 2.4 (m, 4H); 1.9 (d, 2H); 1.4 (m, 4H); 1.1 (t, 6H); 0.8 (t, 3H).

Example 4

N-Methyl-N-phenyl-3-[phenyl(1-propylpiperidin-4-yl)amino]benzamide Fumarate[1:1.4], C4

Following the procedure of Example 1 and employing N-phenyl-1-propyl-4-piperidinamine in place of N-(3-methoxyphenyl)-1-propyl-4-piperidinamine and 3-bromo-N-methylbenzanilide in place of N,N-diethyl-4-bromobenzamide, N,N-diethyl-4-[phenyl(1-propylpiperidin-4-yl)amino]benzamide fumarate [1:1.5] was obtained as the product: mp 190–191° C. MS m/z=428 (M$^+$+H). 300 MHz $^1$H NMR (DMSO-d$_6$) δ7.35 (t, 4H); 7.2–6.9 (m, 4H) 6.55 (t, 2H); 6.5 (s, 2H); 3.85 (m, 1H); 3.3 (s, 3H); 2.9 (d, 2H); 2.4 (t, 2H); 2.2 (d, 2H); 1.6 (d 2H); 1.4 (m, 2H); 1.1 (m, 2H); 0.8 (t, 3H).

Procedure B

Following the protocol of Procedure A and employing the appropriate aryl amine in place of m-anisidine and the requisite N-substituted piperidine in place of N-propylpiperidine, the following N-aryl-1-substituted-4-piperidinamines, I2–I 10, were prepared:

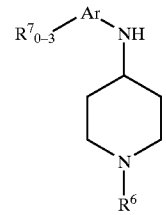

where R$^6$ and R$^7$ are dependently selected from the groups consisting of:

| Cpd# | R$^7$-Ar | R$^6$ | MS m/z (M$^+$ + H) |
|---|---|---|---|
| I1 | 3-CH$_3$O—Ph | 1-Propyl | 249 |
| I2 | 3-Cl—Ph | 1-Propyl | 253 |
| I3 | 2-CH$_3$O—Ph | 1-Propyl | 249 |
| I4 | 1-Naphthyl | 1-Propyl | 269 |
| I5 | Ph | Methyl | 191 |
| I6 | 3-CH$_3$O—Ph | Methyl | 221 |
| I7 | 3-F—Ph | Methyl | 209 |
| I8 | Ph | Ethyl | 205 |
| I9 | 3-F—Ph | Ethyl | 223 |
| I10 | Ph | Benzyl | 267 |

Example 5

Following the procedure of Example 1 and employing the appropriate N-aryl-4-piperidinamine in place of N-(3-methoxyphenyl)-1-propyl-4-piperidinamine and the requisite 4-bromobenzamide in place of N,N-diethyl-4-bromobenzamide, the following compounds C5–C45 were obtained:

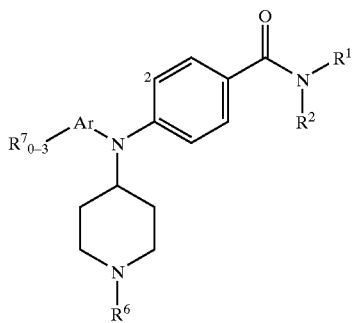

where $R^1$, $R^2$, $R^6$ and $R^7$—Ar are dependently selected from the groups consisting of:

| Cpd# | $R^7$-Ar | $R^6$ | $R^1$ | $R^2$ | MS | Isol'n |
|---|---|---|---|---|---|---|
| C5 | 3-Cl—Ph | 1-Propyl | Ethyl | Ethyl | 428 | A |
| C6 | 3-Cl—Ph | 1-Propyl | —(CH$_2$)$_4$— | | 426 | A |
| C7 | 2-CH$_3$O—Ph | 1-Propyl | Ethyl | Ethyl | 424 | A |
| C8 | 1-Naphthyl | 1-Propyl | Ethyl | Ethyl | 416 | A |
| C9 | 1-Naphthyl | 1-Propyl | —(CH$_2$)$_4$— | | 456 | A |
| C10 | Ph | Methyl | Ethyl | Ethyl | 366 | B |
| C11 | Ph | Methyl | 1-Propyl | 1-Propyl | 394 | B |
| C12 | Ph | Methyl | Methyl | Ethyl | 352 | B |
| C13 | Ph | Methyl | 2-Propyl | 2-Propyl | 394 | B |
| C14 | Ph | Methyl | —(CH$_2$)$_2$—O—(CH$_2$)$_2$— | | 380 | B |
| C15 | Ph | Methyl | —(CH$_2$)$_5$— | | 378 | B |
| C16 | Ph | Methyl | —(CH$_2$)$_4$— | | 364 | B |
| C17 | 3-CH$_3$O—Ph | Methyl | Ethyl | Ethyl | 396 | B |
| C18 | 3-CH$_3$O—Ph | Methyl | 1-Propyl | 1-Propyl | 424 | B |
| C19 | 3-CH$_3$O—Ph | Methyl | Methyl | Ethyl | 382 | B |
| C20 | 3-CH$_3$O—Ph | Methyl | 2-Propyl | 2-Propyl | 424 | B |
| C21 | 3-CH$_3$O—Ph | Methyl | —(CH$_2$)$_2$—O—(CH$_2$)$_2$— | | 410 | B |
| C22 | 3-CH$_3$O—Ph | Methyl | —(CH$_2$)$_5$— | | 408 | B |
| C23 | 3-CH$_3$O—Ph | Methyl | —(CH$_2$)$_4$— | | 394 | B |
| C24 | 3-F—Ph | Methyl | Ethyl | Ethyl | 384 | B |
| C25 | 3-F—Ph | Methyl | 1-Propyl | 1-Propyl | 412 | B |
| C26 | 3-F—Ph | Methyl | Methyl | Ethyl | 370 | B |
| C27 | 3-F—Ph | Methyl | 2-Propyl | 2-Propyl | 412 | B |
| C28 | 3-F—Ph | Methyl | —(CH$_2$)$_2$—O—(CH$_2$)$_2$— | | 398 | B |
| C29 | 3-F—Ph | Methyl | —(CH$_2$)$_5$— | | 396 | B |
| C30 | 3-F—Ph | Methyl | —(CH$_2$)$_4$— | | 382 | B |
| C31 | Ph | Ethyl | Ethyl | Ethyl | 380 | B |
| C32 | Ph | Ethyl | 1-Propyl | 1-Propyl | 408 | B |
| C33 | Ph | Ethyl | Methyl | Ethyl | 366 | B |
| C34 | Ph | Ethyl | 2-Propyl | 2-Propyl | 408 | B |
| C35 | Ph | Ethyl | —(CH$_2$)$_2$—O—(CH$_2$)$_2$— | | 394 | B |
| C36 | Ph | Ethyl | —(CH$_2$)$_5$— | | 392 | B |
| C37 | Ph | Ethyl | —(CH$_2$)$_4$— | | 378 | B |
| C38 | 3-F—Ph | Ethyl | Ethyl | Ethyl | 398 | B |
| C39 | 3-F—Ph | Ethyl | 1-Propyl | 1-Propyl | 426 | B |
| C40 | 3-F—Ph | Ethyl | Methyl | Ethyl | 384 | B |
| C41 | 3-F—Ph | Ethyl | 2-Propyl | 2-Propyl | 426 | B |
| C42 | 3-F—Ph | Ethyl | —(CH$_2$)$_2$—O—(CH$_2$)$_2$— | | 412 | B |
| C43 | 3-F—Ph | Ethyl | —(CH$_2$)$_5$— | | 410 | B |
| C44 | 3-F—Ph | Ethyl | —(CH$_2$)$_4$— | | 396 | B |
| C45 | Ph | Benzyl | Ethyl | Ethyl | 442 | A |

Isolation, Method A: chromatography on SiO$_2$ with CH$_2$Cl$_2$/MeOH/NH$_4$OH; 95/5/0.5.

Method B: Reverse phase HPLC on YMC J' sphere H80 (20/80 MeCN/0.1% aq. TFA to 90/10 MeCN/0.1% aq. TFA)

Example 6

N,N-Diethyl-4-[3-acetoxyphenyl(1-propylpiperidin-4-yl)amino]benzamide Hydrochloride[1:1], C46

A solution of 0.96 g (2.3 mmol) of N,N-diethyl-4-[3-hydroxyphenyl(1-propylpiperidin-4-yl)amino]benzamide was stirred in 20 mL of CH$_2$Cl$_2$ and 0.17 mL of acetyl chloride was added. The mixture was stirred for 2 h. The solvent was evaporated and the residue recrystallized from 2-PrOH to give 0.7 g (62% yield) of the title compound as a white crystalline solid: mp 218–219° C. MS m/z=452 (M$^+$+H). 300 MHz $^1$H NMR (DMSO-d$_6$) δ7.3 (d 2H); 7.2 (m, 1H);6.9 (d, 2H);6.7 (m, 2H);4.1 (t, 3H); 3.6 (d, 2H); 3.4 (m, 4H); 2.8 (m, 4H); 2.4(m, 2H); 2.2(s, 3H) 2.1 (d, 2H); 1.9 (m, 2H); 1.2 (t, 6H), 1.0 (t, 3H). Anal calcd. for C$_{27}$H$_{37}$N$_3$O$_3$.HCl: C, 66.45; H, 7.45; N, 8.61. Found: C, 66.07; H, 7.83; N, 8.32.

Biological Testing

Delta- and mu-opioid receptor binding of the above compounds was determined according to the following procedures and the following results were obtained.

1) High Throughput Screening Assay for Delta-Opioid Receptor Binding

Materials

This is a receptor based screen to detect the competitive binding of test compounds at the opioid delta receptor against the radioligand, [$^3$H]bremazocine (S.A.=25.5 Ci/mmol, Dupont/NEN, Cambridge, Mass.). The receptor is a cloned human cDNA expressed in mammalian CHO cells. Membranes prepared from these cells are purchased from Receptor Biology, Baltimore, Md.). The reaction buffer is composed as follows: HEPES (50 mM final), MgCl.6H$_2$O (5 mM final), o-phenanthroline (20 mg/l), aprotinin (10 mg/l), Pefabloc SC (250 mg/l), leupeptin (0.5 mg/l, pepstatin A (0.7 mg/l), trypsin inhibitor (25 mg/l), chymostatin (10 mg/l), pH=7.2. Naloxone, 10 uM, is used to define non-specific binding. The assay employs filtration to capture receptor and bound ligand.

Procedure

The receptor (membrane) preparation (28 ug protein) is allowed to incubate with the opioid receptor radioligand ([$^3$H]bremazocine, 2.4 nM) in 96-well plates until equilibrium is reached (>2 hr). Following incubation with the radioligand at 23° C., the well contents are filtered onto 96-well Whatman GF/C filter plates using a Packard cell harvester. Radioligand bound to the receptor also remains on the filter. The filters are rinsed three times with 0.5 mL of physiological saline (0.9% NaCl) to remove any unbound radioligand from the filters. Filters are dried and scintillation fluid is then added to the filters which emits light in proportion to the amount of radioactivity on the filter which is determined using an Packard Topcount scintillation counter.

Principle

Unknown drugs included in the incubation which bind to the same receptor as the radioligand will compete for the receptor and reduce the amount of radioligand which binds to the receptor. This is detected as a decreased scintillation signal from that particular incubation. The better an unknown competes for the receptor, the larger the observed decrease in radioligand bound to the receptor; thus the assay is in the format of an inhibition study. Data are reported as percent inhibition of control binding.

Results

The following compounds were tested with the following results.

| Cpd# | % I @ 25 μM | Cpd# | % I @ 25 μM |
|---|---|---|---|
| C1 | 97 | C11 | 101 |
| C3 | 94 | C12 | 95 |
| C4 | 41 | C13 | 100 |

-continued

| Cpd# | % I @ 25 μM | Cpd# | % I @ 25 μM |
| --- | --- | --- | --- |
| C5 | 102 | C14 | 93 |
| C6 | 101 | C15 | 68 |
| C7 | 100 | C16 | 81 |
| C8 | 69 | C17 | 98 |
| C9 | 103 | C18 | 100 |
| C10 | 100 | C19 | 95 |
| C20 | 98 | C34 | 100 |
| C21 | 70 | C35 | 64 |
| C22 | 89 | C36 | 92 |
| C23 | 91 | C37 | 88 |
| C24 | 97 | C38 | 98 |
| C25 | 100 | C39 | 101 |
| C26 | 96 | C40 | 97 |
| C27 | 97 | C41 | 88 |
| C28 | 77 | C42 | 64 |
| C29 | 85 | C43 | 89 |
| C30 | 85 | C44 | 87 |
| C31 | 100 | C45 | 99 |
| C32 | 100 | C46 | 100 |
| C33 | 98 | | |

2) Manual Tissue Screening Assay for Delta- and Mu-Opioid Receptor Binding

A) Rat Brain δ-Opioid Receptor Binding Assay

Procedure

Male, Wistar rats (150–250 g, VAF, Charles River, Kingston, N.Y.) are killed by cervical dislocation, and their brains removed and placed immediately in ice cold Tris HCl buffer (50 mM, pH 7.4). The forebrains are separated from the remainder of the brain by a coronal transection, beginning dorsally at the colliculi and passing ventrally through the midbrain-pontine junction. After dissection, the forebrains are homogenized in Tris buffer in a Teflon®-glass homogenizer. The homogenate is diluted to a concentration of 1 g of forebrain tissue per 100 mL Tris buffer and centrifuged at 39,000× G for 10 min. The pellet is resuspended in the same volume of Tris buffer with several brief pulses from a Polytron homogenizer. This particulate preparation is used for the δ-opioid binding assays. Following incubation with the δ-selective peptide ligand [$^3$H]DPDPE at 25° C., the tube contents filtered through Whatman GF/B filter sheets on a Brandel cell harvester. The tubes and filters are rinsed three times with 4 mL of 10 mM HEPES (pH7.4), and the radioactivity associated with the filter circles determined using Formula 989 scintillation fluid (New England Nuclear, Boston, Mass.) in a scintillation counter.

Analysis

The data are used to calculate either the % inhibition compared to control binding (when only a single concentration of test compound is evaluated) or a $K_i$ value (when a range of concentrations is tested).

% inhibition is calculated as: 1−(test compound dpm-nonspecific dpm)/(total dpm−nonspecific dpm)* 100

$K_i$ values are calculated using the LIGAND (Munson, P. J. and Rodbard, D., Anal. Biochem. 107: 220–239, 1980) data analysis program.

B) Rat Brain μ-Opioid Receptor Binding Assay

Procedure

Male, Wistar rats (150–250 g, VAF, Charles River, Kingston, N.Y.) are killed by cervical dislocation, and their brains removed and placed immediately in ice cold Tris HCl buffer (50 mM, pH 7.4). The forebrains are separated from the remainder of the brain by a coronal transection, beginning dorsally at the colliculi and passing ventrally through the midbrain-pontine junction. After dissection, the forebrains are homogenized in Tris buffer in a Teflon®-glass homogenizer. The homogenate is diluted to a concentration of 1 g of forebrain tissue per 100 mL Tris buffer and centrifuged at 39,000× G for 10 min. The pellet is resuspended in the same volume of Tris buffer with several brief pulses from a Polytron homogenizer. This particulate preparation is used for the μ-opioid binding assays. Following incubation with the m-selective peptide ligand [$^3$H]DAMGO at 25° C., the tube contents are filtered through Whatman GF/B filter sheets on a Brandel cell harvester. The tubes and filters are rinsed three times with 4 mL of 10 mM HEPES (pH7.4), and the radioactivity associated with the filter circles determined using Formula 989 scintillation fluid (New England Nuclear, Boston, Mass.) in a scintillation counter.

Analysis

The data are used to calculate either the % inhibition compared to control binding (when only a single concentration of test compound is evaluated) or a $K_i$ value (when a range of concentrations is tested).

% inhibition is calculated as: 1−(test compound dpm-nonspecific dpm)/(total dpm−nonspecific dpm)* 100

$K_i$ values are calculated using the LIGAND (Munson, P. J. and Rodbard, D., Anal. Biochem. 107: 220–239, 1980) data analysis program.

Results

N,N-Diethyl-4-[phenyl(1-propylpiperidin-4-yl)amino]benzamide fumarate, C4, exhibited a $K_i$ of 25 nM in binding to the δ-opioid receptor and a $K_i$ of 153 nM in binding to the μ-opioid receptor. N,N-Diethyl-4-[3-hydroxyphenyl(1-propylpiperidin-4-yl)amino]benzamide fumarate, C2, exhibited a $K_i$ of 0.83 nM in binding to the δ-opioid receptor and a $K_i$ of 2,762 nM in binding to the μ-opioid receptor.

The activity of compounds of the invention as analgesics may be demonstrated by the mouse acetylcholine-bromide induced constriction assay as described below:

C) Mouse Acetylcholine Bromide-Induced Abdominal Constriction Assay

Procedure

The mouse acetylcholine-induced abdominal constiction assay, as described by Collier et al. in *Brit. J. Pharmacol. Chem. Ther.,* 32: 295–310, 1968, with minor modifications was used to assess analgesic potency of the compounds of formula (I). The test drugs or appropriate vehicles were administered orally (p.o.) and 30 minutes later the animal received an intraperitoneal (i.p.) injection of 5.5 mg/kg acetylcholine bromide (Matheson, Coleman and Bell, East Rutherford, N.J.). The mice were then placed in groups of three into glass bell jars and observed for a ten minute observation period for the occurrence of an abdominal constriction response (defined as a wave of constriction and elongation passing caudally along the abdominal wall, accompanied by a twisting of the trunk and followed by extension of the hind limbs). The percent inhibition of this response to a nociceptive stimulus (equated to % analgesia) was calculated as follows: The % inhibition of response, i.e., % analgesia is equal to the difference between the No. of control animal responses and the No. of drug-treated animal responses times 100 divided by the No. of control animals responding.

Results

N,N-Diethyl-4-[phenyl(1-propylpiperidin-4-yl)amino]benzamide fumarate, C4, exhibited an $ED_{50}$ of 4.2 μmol/kg in this assay.

What is claimed is:

1. A compound which binds to the delta-opioid receptor and which is an effective analgesic of the formula:

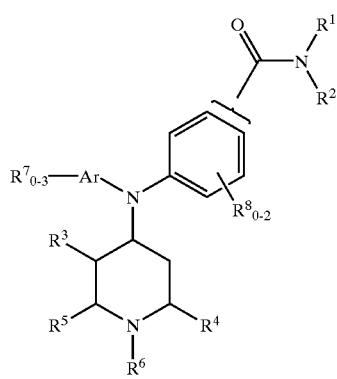

where
- Ar is phenyl, 1-naphthyl or 2-naphthyl, each optionally substituted with 1 to 3 $R^7$;
- $R^1$ and $R^2$ are independently selected from the group consisting of hydrogen, $C_{1-8}$alkyl; and benzyl, optionally mono-, di-, or tri-substituted with halo, $C_{1-6}$alkyl, $C_{1-6}$alkoxy or trifluoromethyl;
- $R^3$, $R^4$ and $R^5$ are independently selected from hydrogen and $C_{1-4}$alkyl;
- $R^6$ is phenyl$C_{2-4}$alkyl, where the phenyl is mono-, di-, or tri-substituted with $R^7$;
- $R^7$ is independently selected from the group consisting of hydroxy, halo, $C_{1-3}$alkyl, trifluoromethyl and $C_{1-3}$alkoxy and two $R^7$ can together may form a single moiety which is —O(CH$_2$)$_{1-3}$O— attached to adjacent carbon atoms of $R^6$ with the proviso that where $R^7$ is a substitutent on $R^6$, then it may not be $C_{1-3}$alkyl; and
- $R^8$ is independently selected from the group consisting of halo, $C_{1-6}$alkyl, $C_{1-6}$alkoxy and trifluoromethyl.

2. The compound of claim 1 wherein Ar is phenyl.

3. The compound of claim 1 wherein $R^1$ and $R^2$ are independently selected from the group consisting of hydrogen, methyl, ethyl, n-propyl, i-propyl, n-butyl, t-butyl, i-butyl, phenyl, p-chlorophenyl, p-fluorophenyl, p-methylphenyl, p-trifluoromethylphenyl, benzyl, p-chlorobenzyl, p-fluorobenzyl, p-methylbenzyl and p-trifluoromethylbenzyl, or alternatively, $R^1$ and $R^2$ are taken together with their N of attachment to form a ring which is selected from the group consisting of pyrrolidinyl and piperidinyl.

4. The compound of claim 1 wherein $R^3$, $R^4$ and $R^5$ are independently selected from hydrogen, methyl, ethyl, n-propyl, i-propyl and t-butyl.

5. The compound of claim 1 wherein $R^7$ are independently selected from the group consisting of hydroxy, chloro, bromo, fluoro, methyl, ethyl, n-propyl, i-propyl, n-butyl, i-butyl, t-butyl, methoxy, ethoxy, formyl, acyl, acetoxy, cyano, amino, methylamido, methylamino, N,N-dimethylamino, methylthio, methylsulfonyl, trifluoromethoxy and trifluoromethyl, and preferred moieties where two $R^7$ together form a single moiety are selected from the group consisting of propylene, butylene and —OCH$_2$O—.

6. The compound of claim 1 wherein $R^8$ are independently selected from the group consisting of chloro, bromo, fluoro, methyl, ethyl, n-propyl, i-propyl, t-butyl, methoxy, ethoxy and trifluoromethyl.

7. The compound of claim 1 having the general structure:

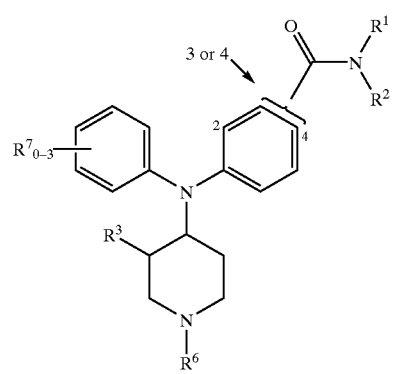

where $R^1$, $R^2$, $R^3$, $R^6$ and $R^7$ are independently selected from the groups consisting of:

| Cpd # | $R^7$ | $R^6$ | $R^1$ | $R^2$ | amide subst. | $R^3$ |
|---|---|---|---|---|---|---|
| P93 | none | ⌁-C$_6$H$_3$(OMe)(OMe) | —CH$_2$CH$_3$ | —CH$_2$CH$_3$ | 4 | H |
| P94 | m-F | ⌁-C$_6$H$_3$(OMe)(OMe) | —CH$_2$CH$_3$ | —CH$_2$CH$_3$ | 4 | H |
| P95 | m-sCH$_3$ | ⌁-C$_6$H$_3$(OMe)(OMe) | —CH$_3$ | —CH$_2$CH$_3$ | 4 | ci-Me |

-continued
| Cpd # | R⁷ | R⁶ | R¹ | R² | amide subst. | R³ |
|---|---|---|---|---|---|---|
| P96 | none | 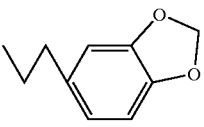 | —CH₂CH₃ | —CH₂CH₃ | 4 | H |
| P97 | m-oCH₃ | 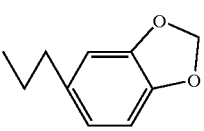 | -nC₃H₇ | -nC₃H₇ | 4 | H |
| P98 | m-OH | 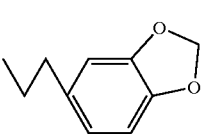 | —CH₃ | —CH₂CH₃ | 4 | tr-Me |
| P102 | none | 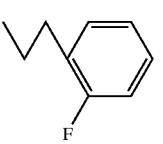 | —CH₂CH₃ | —CH₂CH₃ | 4 | H |
| P103 | p-OH | 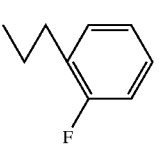 | —CH₂CH₃ | -nC₃H₇ | 4 | H |
| P104 | p-F | 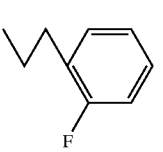 | -nC₃H₇ | -nC₃H₇ | 4 | tr-Me |
| P108 | none | 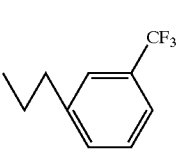 | —CH₂CH₃ | —CH₂CH₃ | 4 | H |
| P109 | m-CH₃ | 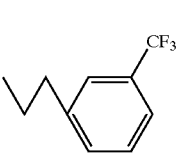 | —CH₃ | —CH₂CH₃ | 4 | H |

-continued

| Cpd # | R⁷ | R⁶ | R¹ | R² | amide subst. | R³ |
|---|---|---|---|---|---|---|
| P110 | 2,3-oCH₃ | 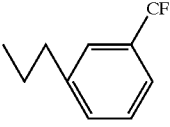 | —CH₃ | -nC₃H₇ | 4 | H |

8. A method for the treatment of pain in mammals comprising administering an effective amount of a compound of the formula:

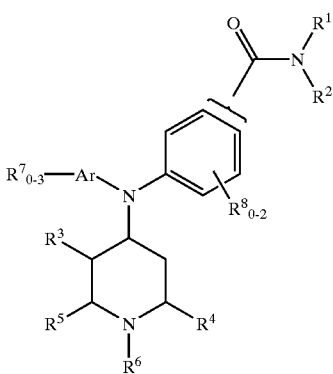

I where

Ar is phenyl, 1-naphthyl or 2-naphthyl, each optionally substituted with 1 to 3 $R^7$;

$R^1$ and $R^2$ are independently selected from the group consisting of hydrogen, $C_{1-8}$alkyl; and benzyl, optionally mono-, di-, or tri-substituted with halo, $C_{1-6}$alkyl, $C_{1-6}$alkoxy or trifluoromethyl;

$R^3$, $R^4$ and $R^5$ are independently selected from hydrogen and $C_{1-4}$alkyl;

$R^6$ is phenyl$C_{2-4}$alkyl, where the phenyl is mono-, di-, or tri-substituted with $R^7$;

$R^7$ is independently selected from the group consisting of hydroxy, halo, $C_{1-3}$alkyl, trifluoromethyl and $C_{1-3}$alkoxy and two $R^7$ can together may form a single moiety which is —O(CH₂)₁₋₃O— attached to adjacent carbon atoms of $R^6$ with the proviso that where $R^7$ is a substitutent on $R^6$, then it may not be $C_{1-3}$alkyl; and $R^8$ is independently selected from the group consisting of halo, $C_{1-6}$alkyl, $C_{1-6}$alkoxy and trifluoromethyl.

* * * * *